United States Patent
Shaarabany

(10) Patent No.: US 12,239,769 B2
(45) Date of Patent: Mar. 4, 2025

(54) MULTI-FUNCTION AIR PURIFYING AND STERILIZING SYSTEM

(71) Applicant: Effy Shaarabany, Ramat-Gan (IL)

(72) Inventor: Effy Shaarabany, Ramat-Gan (IL)

( * ) Notice: Subject to any disclaimer, the term of this patent is extended or adjusted under 35 U.S.C. 154(b) by 159 days.

(21) Appl. No.: 17/926,786

(22) PCT Filed: May 27, 2021

(86) PCT No.: PCT/IL2021/050627
§ 371 (c)(1),
(2) Date: Nov. 21, 2022

(87) PCT Pub. No.: WO2021/240526
PCT Pub. Date: Dec. 2, 2021

(65) Prior Publication Data
US 2023/0241280 A1    Aug. 3, 2023

Related U.S. Application Data

(60) Provisional application No. 63/041,867, filed on Jun. 20, 2020, provisional application No. 63/030,683, filed on May 27, 2020.

(51) Int. Cl.
*A61L 9/22* (2006.01)
*A61L 9/20* (2006.01)
(Continued)

(52) U.S. Cl.
CPC ............... *A61L 9/22* (2013.01); *A61L 9/20* (2013.01); *B01D 53/007* (2013.01);
(Continued)

(58) Field of Classification Search
None
See application file for complete search history.

(56) References Cited

U.S. PATENT DOCUMENTS

| 4,223,598 A | 9/1980 | Suzuki et al. |
| 6,877,724 B1 * | 4/2005 | Petty ................ A61L 9/04 |
| | | 261/78.2 |

(Continued)

FOREIGN PATENT DOCUMENTS

| CN | 1216253 C | * | 8/2005 |
| CN | 202044554 U | | 11/2011 |

(Continued)

OTHER PUBLICATIONS

PCT International Search Report for International Application No. PCT/IL2021/050627, mailed Aug. 29, 2021, 5pp.

(Continued)

*Primary Examiner* — Andrew Smyth
(74) *Attorney, Agent, or Firm* — The Roy Gross Law Firm, LLC; Roy Gross

(57) ABSTRACT

A multi-function air purifying and sterilizing system for filtering and/or sterilizing air comprises: (a) a casing having an air inlet at one end of the casing and an air outlet at the other end of the casing, (b) electrostatic means for attracting particulate matter including biological contaminants, and thus, for removing the particulate matter and the biological contaminants from an air stream passing therethrough, the electrostatic means comprising at least one spiked surface, the at least one spiked surface inducing corona discharge and/or cold plasma when high voltage is applied, the corona discharge and/or the cold plasma producing ozone molecules, (c) at least one energy source for producing rays, the at least one energy source is inter-displaced within the electrostatic means to have the produced rays in close proximity to the electrostatic means for maximizing the at least one energy source efficiency in demolishing the particulate matter and the biological contaminants depositing on the electrostatic means, and/or converting the ozone molecules to hydroxyl radicals, the hydroxyl radicals disin- (Continued)

fecting and inhibiting the biological contaminants and/or odors, and/or gases in the air stream, the hydroxyl radicals is spreadable within a confined space, thus, disinfecting biological contaminants and/or odors, and/or gases within a confined space.

18 Claims, 12 Drawing Sheets

(51) Int. Cl.
    *B01D 53/00*     (2006.01)
    *B01D 53/32*     (2006.01)
    *B03C 3/36*     (2006.01)
    *B03C 3/38*     (2006.01)
    *B03C 3/41*     (2006.01)
    *B03C 3/49*     (2006.01)
    *F24F 1/0076*     (2019.01)
    *F24F 8/22*     (2021.01)
    *F24F 8/30*     (2021.01)
    *F24F 8/40*     (2021.01)
    *F24F 11/39*     (2018.01)

(52) U.S. Cl.
    CPC ............ *B01D 53/323* (2013.01); *B03C 3/368* (2013.01); *B03C 3/38* (2013.01); *B03C 3/41* (2013.01); *B03C 3/49* (2013.01); *F24F 1/0076* (2019.02); *F24F 8/22* (2021.01); *F24F 8/30* (2021.01); *F24F 8/40* (2021.01); *F24F 11/39* (2018.01); *A61L 2209/111* (2013.01); *A61L 2209/12* (2013.01); *A61L 2209/212* (2013.01); *B01D 2251/104* (2013.01); *B01D 2257/91* (2013.01); *B01D 2258/06* (2013.01); *B01D 2259/818* (2013.01); *B03C 2201/10* (2013.01)

(56) References Cited

U.S. PATENT DOCUMENTS

| | | |
|---|---|---|
| 2007/0041882 A1 | 2/2007 | Roseberry et al. |
| 2007/0107597 A1 | 5/2007 | Cheung |
| 2007/0212273 A1* | 9/2007 | Edwards ................ F24F 8/192 422/186.3 |
| 2008/0093210 A1* | 4/2008 | Edwards .............. B01D 53/007 422/186.3 |
| 2014/0314627 A1 | 10/2014 | Morneault |
| 2015/0017059 A1* | 1/2015 | Arlemark ................ A61L 9/015 422/119 |
| 2018/0250431 A1 | 9/2018 | Eide et al. |

FOREIGN PATENT DOCUMENTS

| | | |
|---|---|---|
| CN | 102430328 A | 5/2012 |
| CN | 108534265 A | 9/2018 |
| JP | H09253189 A | 9/1997 |
| JP | 2015051268 A | 3/2015 |
| KR | 100786710 B1 | 12/2007 |
| KR | 20180132290 A | 12/2018 |
| WO | 2018234633 A1 | 12/2018 |

OTHER PUBLICATIONS

PCT Written Opinion for International Application No. PCT/IL2021/050627, mailed Aug. 29, 2021, 6pp.
PCT International Preliminary Report on Patentability for International Application No. PCT/IL2021/050627, issued Nov. 17, 2022.
European Patent Office, Supplementary European Search Report for European Patent Application No. 21813391, dated Nov. 2, 2023, 8pp.

* cited by examiner

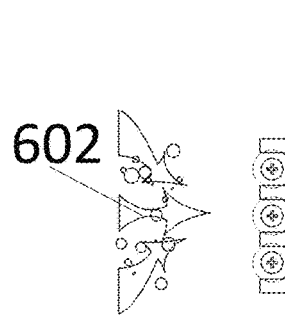
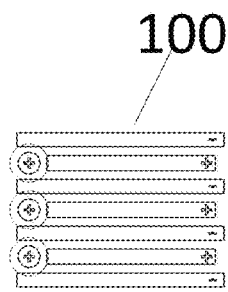
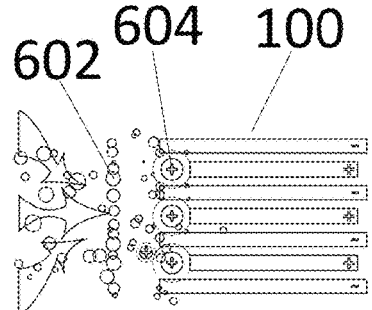
Fig. 6A
Fig. 6B
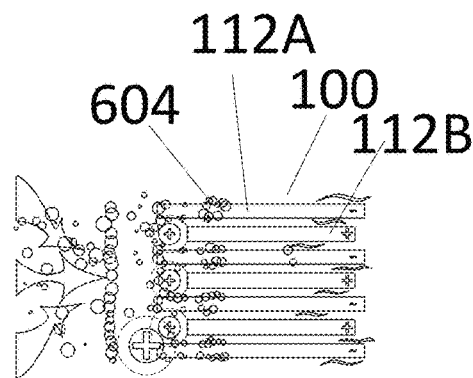
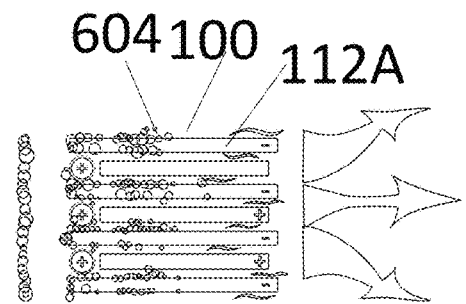
Fig. 6C
Fig. 6D
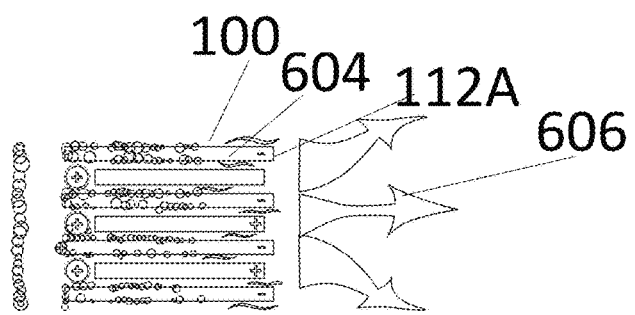
Fig. 6E

MULTI-FUNCTION AIR PURIFYING AND STERILIZING SYSTEM

CROSS REFERENCE TO RELATED APPLICATIONS

This application is a National Phase of PCT Patent Application No. PCT/IL2021/050627 having International filing date of May 27, 2021, which claims the benefit of priority of U.S. Provisional Patent Application No. 63/030,683, filed May 27, 2020 and U.S. Provisional Patent Application No. 63/041,867, filed Jun. 20, 2020, the contents of which are all incorporated herein by reference in their entirety.

FIELD OF THE INVENTION

The present technology relates generally to air flows filters. More specifically, the present invention relates to high efficiency air-purification and sterilization devices.

BACKGROUND

Air pollution is a significant risk factor for a number of pollution-related diseases, including respiratory infections, heart disease, stroke and lung cancer. Poor air quality affects the body's respiratory system and the cardiovascular system, and individual reactions to air pollutants depend on the type of pollutant a person is exposed to, the degree of exposure, and the individual's health status and genetics.

Indoor air pollution and poor urban air quality are known as two of the world's worst toxic pollution problems. Air pollution particles can be solid, liquid, or gases. Excess particles can build up indoors, in confined places such as busses/trains/aircrafts cabins, and the like due to inadequate ventilation, high temperature, and high humidity levels. Ventilation may aid in decreasing indoor pollutant levels, but at the same time may enable outdoor pollutants to travel indoors.

Thus, if the living environment is prone to indoor air pollution, an air purifier shall be helpful to remove harmful particles and improve the air quality.

Various air purifiers are available nowadays some of which are described as follow:

KR20180132290 describes an air sterilizer performing a humidification function of supplying water required in a photocatalyst from a photocatalytic filter device, removing dust by using a capillary filter, sterilizing air by using a UV lamp, removing various malodors by using the photocatalytic filter device reacting to UV lays, and collecting fine dust by using an electrical precipitator of a fine mesh to discharge sterilized air by an exhaust fan. The air sterilizer has a combination of sterilizing, photocatalytic and electric dust collecting functions by humidification and UV rays.

CN202044554 discloses an air sterilizing purifier that structurally comprises a housing, an air inlet pipe and an air outlet, wherein a dust collector is mounted at the bottom of the shell; the air inlet pipe is arranged at the bottom of the dust collector; an electrode wire is arranged on the side wall of the dust collector; an ultraviolet (UV) sterilization lamp is arranged in the housing; a spiral electrode ring is arranged on the periphery of the ultraviolet sterilization lamp; and the air outlet is formed at the top of the shell.

KR100786710 describes an electric precipitator which improves the charging efficiency of fine dust included in the polluted air by generating high discharge current with low voltage by an ionizing unit provided with a discharge electrode having needle-shaped projections formed on both sides.

As noted above, various designs of air purifiers have been developed over the years, however, such designs lack the ability to assure a sufficient time duration necessary for destruction of active micro-organisms, thus there is still a need for improved air sterilizers. Therefore, it is an aim of the present invention to provide an air purifier which, not only provides noticeable high filtering characteristics, but also allows a substantial time duration required for demolishing of harmful bacteria, viruses and other active micro-organisms for ensuring high quality of air in a living environment.

SUMMARY OF THE INVENTION

The multi-function air purifying system of the present invention is intended for use in both indoor and outdoor spaces. More specifically, the multi-function purifying system may be used to sterilize incoming and circulating air in rooms, halls, as well as in various confined spaces, such as, in busses, trains and hospital wards. It may also be used to filter and purify outcoming air originated via kitchens stoves, fryers and factory polluting halls/machines, and it may also be used in outdoor areas such as hospital outer areas and the like.

The multi-function air purifying system of the present invention is advantageous for: (a) providing a remarkable high filtering efficiency—a relatively high efficiency of 95% and higher in filtering particles having a diameter of 0.01 microns and higher and (b) assuring that micro-organisms are captured and retained within the purifying system for a time duration sufficient to guarantee their destruction, i.e., at least 2 minutes, or more precisely, an unlimited time duration.

In accordance with some embodiments of the present invention, there is thus provided a multi-function air purifying and sterilizing system for filtering and/or sterilizing air comprising:

a casing having an air inlet at one end of the casing and an air outlet at the other end of the casing, electrostatic means for attracting particulate matter including biological contaminants, and thus, for removing said particulate matter and said biological contaminants from an air stream passing therethrough, said electrostatic means comprising at least one spiked surface, said at least one spiked surface inducing corona discharge and/or cold plasma when high voltage is applied, said corona discharge and/or said cold plasma producing ozone molecules, at least one energy source for producing rays, said at least one energy source is inter-displaced within said electrostatic means to have the produced rays in close proximity to said electrostatic means for:

(a) maximizing said at least one energy source efficiency in demolishing said particulate matter and said biological contaminants depositing on said electrostatic means, and/or (b) converting said ozone molecules to hydroxyl radicals, said hydroxyl radicals disinfecting and inhibiting said biological contaminants in said air stream, said hydroxyl radicals is spreadable within a confined space, thus, disinfecting biological contaminants within a confined space, thereby, said multi-function air purifying and sterilizing system ether filtering and sterilizing the air via said electrostatic means and/or producing ozone molecules convertible to hydroxyl radicals for disinfecting and inhibiting said biological contaminants in said air stream and in said confined space.

Furthermore, in accordance with some embodiments of the present invention, there is provided a multi-function air purifying and sterilizing system for sterilizing air comprising:

a casing having an air inlet at one end of the casing and an air outlet at the other end of the casing, electrostatic means comprising at least one spiked surface, said at least one spiked surface inducing corona discharge and/or cold plasma when high voltage is applied, said corona discharge producing ozone molecules, at least one energy source for producing rays, said at least one energy source is inter-displaced within said electrostatic means to have the produced rays in close proximity to said electrostatic means for converting said ozone molecules to hydroxyl radicals, said hydroxyl radicals disinfecting and inhibiting biological contaminants, and/or odors, and/or gases.

thereby, said multi-function air purifying and sterilizing system producing ozone molecules convertible to hydroxyl radicals for disinfecting and inhibiting biological contaminants, and/or odors, and/or gases.

Furthermore, in accordance with some embodiments of the present invention, the hydroxyl radicals acting as a strong oxidizing agent and thus eliminating micro-organisms that are active and capable of developing and multiplying on said electrostatic means and/or within a room/confined space, and breaking down a broad range of odors and pathogens.

Furthermore, in accordance with some embodiments of the present invention, the at least one energy source is selected from an ultraviolet source, an X-ray source, a Gamma-ray source, and an Alpha-ray source.

Furthermore, in accordance with some embodiments of the present invention, the at least one ultraviolet source is an ultraviolet lamp arranged in a way that its longitudinal direction is orthogonal to the direction of said air stream.

Furthermore, in accordance with some embodiments of the present invention, the electrostatic means is comprised of a series of electrostatic members, configured parallel to the direction of the air stream, each of said electrostatic members having at least one opening to allow said at least one ultraviolet lamp to be disposed therethrough.

Furthermore, in accordance with some embodiments of the present invention, the electrostatic members comprising electrostatic members operating at a first voltage/collecting members and electrostatic members operating at a second voltage/repelling members.

Furthermore, in accordance with some embodiments of the present invention, the electrostatic members operating at a first voltage/collecting members and said electrostatic members operating at a second voltage/repelling members reflecting the UV light emitting from the at least one light lamp, thus, increasing the intensity of said UV light which in turn increasing the efficiency of demolishing the biological contaminants depositing on said reflective-type collective members and/or increasing the efficiency of converting said ozone molecules to hydroxyl radicals.

Furthermore, in accordance with some embodiments of the present invention, the multi-function air purifying and sterilizing system further comprises multiple ionization wires situated in front of said electrostatic members, and wherein multiple of said electrostatic members operating at a first voltage/collecting members having an extended width to operate with the high voltage ionization wires, and thus, to create an electric field, said electric field charging said air molecules, said particulate matter, and said biological contaminants with a positive charge at an entrance to said multi-function air purifying and sterilizing system.

Furthermore, in accordance with some embodiments of the present invention, the electrostatic members are made of reflective materials.

Furthermore, in accordance with some embodiments of the present invention, the electrostatic members are made of metal, metal alloy, chargeable polymeric material (s) or a combination thereof.

Furthermore, in accordance with some embodiments of the present invention, the electrostatic members operating at a first voltage/collecting members and said electrostatic members operating at a second voltage/repelling members are arranged in an alternating manner to create an electric field powerful enough to direct said charged particulate matter and said charged biological contaminants towards said electrostatic members operating at a first voltage/said collecting members.

Furthermore, in accordance with some embodiments of the present invention, the charged particulate matter and the charged biological contaminants are electrostatically attracted to and thus electrically coupled to said electrostatic members operating at a first voltage/said collecting members.

Furthermore, in accordance with some embodiments of the present invention, the multiple ionization wires and said electrostatic members operating at a first voltage/said collecting members operating at a high voltage, said high voltage producing ozone convertible to an hydroxyl radical via the UV light, said hydroxyl radical disinfects and inhibits biological contaminants.

Furthermore, in accordance with some embodiments of the present invention, at least one opening in each of said electrostatic members operating at a first voltage/said collecting members having a smooth surface.

Furthermore, in accordance with some embodiments of the present invention, the at least one opening in each of said electrostatic members operating at a second voltage/said repelling members having said at least one spiked surface, said at least one spiked surface inducing corona discharge and/or cold plasma when high voltage is applied, said corona discharge producing ozone convertible to an hydroxyl radical via the UV light, said hydroxyl radical disinfects and inhibits biological contaminants.

Furthermore, in accordance with some embodiments of the present invention, each of said at least one opening in each of said electrostatic members operating at a first voltage/said collecting members and each of said electrostatic members operating at a second voltage/said repelling members having a first opening through which a first spacer is disposed and a second opening through which a second spacer is disposed, said first spacer is delivering a first voltage to said electrostatic members operating at a second voltage/said repelling members and said second spacer is delivering a second voltage to said electrostatic members operating at a first voltage/said collecting members, wherein said first opening in said electrostatic members operating at a first voltage/said collecting members is larger than said first opening in electrostatic members operating at a second voltage/said repelling members, so that when said first spacer passes through said first opening in said electrostatic members operating at a first voltage/said collecting members and through said first opening in said electrostatic members operating at a second voltage/said repelling members, said first spacer physically contacts said electrostatic members operating at a second voltage/said repelling member only, and thus transfers the first voltage to said electrostatic members operating at a second voltage/said repelling member only, and wherein said second opening in said electrostatic members operating at a second voltage/said repelling members is larger than said second opening in said electrostatic members operating at a first voltage/collecting members, so that when said second spacer passes through said second opening in said electrostatic members operating at a second voltage/said repelling members and through said second opening in said electrostatic members operating at a first voltage/said collecting members, said second spacer physically contacts said electrostatic members operating at a first voltage/said collecting member only, and thus transfers the second voltage to said electrostatic members operating at a first voltage/said collecting member only.

Furthermore, in accordance with some embodiments of the present invention, the electrostatic members operating at a first voltage/said collecting members are grounded and said electrostatic members operating at a second voltage/repelling members are plates operating at a predefined voltage.

Furthermore, in accordance with some embodiments of the present invention, the casing is a cylindrical conducting tube, said electrostatic means is an electrostatic precipitator comprised of a collecting cylindrical tube and a repelling means.

Furthermore, in accordance with some embodiments of the present invention, the at least one energy source is selected from an ultraviolet source, an X-ray source, a Gamma-ray source, and an Alpha-ray source.

Furthermore, in accordance with some embodiments of the present invention, the at least one energy source is disposed along said cylindrical tube and generating rays which demolish said biological contaminants depositing on the collecting cylindrical tube and/or converting said ozone molecules to hydroxyl radicals.

Furthermore, in accordance with some embodiments of the present invention, the repelling means is at least one ionization rod enveloping the ultraviolet lamp.

Furthermore, in accordance with some embodiments of the present invention, the at least one ionization rod charging air molecules, said particulate matter and said biological contaminants in an air stream as said air stream entering into the multi-function air purifying and sterilizing system.

Furthermore, in accordance with some embodiments of the present invention, the collecting cylindrical tube operating at a first electrical potential and the at least one rod operating at a second electrical potential different from the collecting cylindrical tube to create an electric field, said electric field directing said charged particulate matter and said charged biological contaminants towards said collecting cylindrical tube, and thus, separating said charged particulate matter and said charged biological contaminants from the air stream flowing through the cylinder-shaped multi-function air purifying and sterilizing system.

Furthermore, in accordance with some embodiments of the present invention, ozone is produced via said collecting cylindrical tube and said at least one ionization rod enveloping said energy source, said energy source turning said ozone into a hydroxyl radical which demolishes biological contaminants.

Furthermore, in accordance with some embodiments of the present invention, the collecting cylindrical tube and the at least one rod reflecting the UV light emitted via the light lamp, and thus, increasing the intensity of the UV light hitting the biological contaminants deposits, and thus, increasing the efficiency of sterilization.

Furthermore, in accordance with some embodiments of the present invention, the collecting cylindrical tube and/or said at least one ionization rod is made of metal, metal alloy, chargeable polymeric material (s) or a combination thereof.

Furthermore, in accordance with some embodiments of the present invention, the collecting cylindrical tube and/or said at least one ionization rod is made of reflective materials.

Furthermore, in accordance with some embodiments of the present invention, the multi-function air purifying system further comprising an internal/external air blower disposed in front of/behind said multi-function air purifying and sterilizing system for pushing/pulling air in/out of said multi-function air purifying and sterilizing system.

Furthermore, in accordance with some embodiments of the present invention, the multi-function air purifying and sterilizing system further comprising at least one of a heating, cooling, drying and humidifying means either externally or internally to improve the efficiency of the multi-function air purifying and sterilizing system.

Furthermore, in accordance with some embodiments of the present invention, the multi-function air purifying and sterilizing system further comprising at least one sensor for detecting malfunctions in said blower and/or in at least one of said heating, cooling, drying and humidifying means.

Furthermore, in accordance with some embodiments of the present invention, the multi-function air purifying and sterilizing system further comprising at least one sensor for warning of a burned-out UV sterilization lamp.

Furthermore, in accordance with some embodiments of the present invention, the multi-function air purifying and sterilizing system further comprising at least one sensor for warning of a clogged multi-function air purifying and sterilizing system.

Furthermore, in accordance with some embodiments of the present invention, the multi-function air purifying and sterilizing system removing particulate matter and demolishing biological contaminants having a diameter as small as 0.01 micron.

BRIEF DESCRIPTION OF THE INVENTION

FIG. 1A illustrates a multi-function air purifying system in accordance with some embodiments of the present invention.

FIG. 1B is a top view of the multi-function air purifying system in accordance with some embodiments of the present invention.

FIGS. 2A&B illustrate a collecting plate and a repelling plate in accordance with some embodiments of the present invention.

FIG. 3A illustrates a cylinder-shaped opening created by arranging a plurality of plates in a consecutive order.

FIG. 3B illustrates the cylinder-shaped opening and an ultraviolet sterilization lamp disposed therein.

FIG. 4 is a side-view of the multi-function air purifying system in accordance with some embodiments of the present invention.

FIG. 5 illustrates a blower disposed in front of the multi-function air purification system in accordance with some embodiments of the present invention.

FIGS. 6A-E illustrates an air purifying process via the multi-function air purification system in accordance with some embodiments of the present invention.

DETAILED DESCRIPTION

Figure 1A:
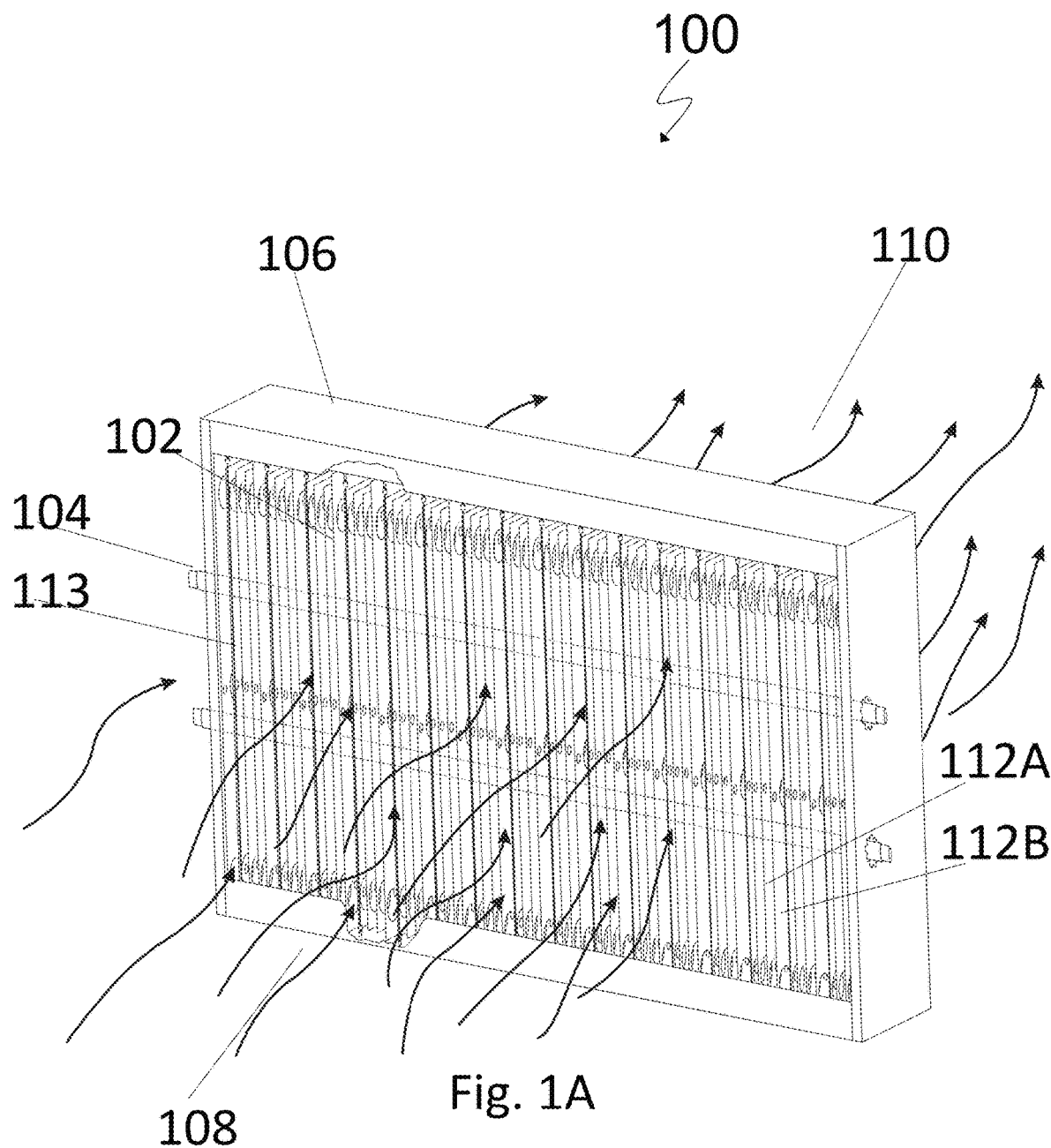

FIG. 1A illustrates a multi-function air purifying and sterilizing system 100 in accordance with some embodiments of the present invention.

The multi-function air purifying and sterilizing system 100 is comprised of electrostatic filtering means 102 and at least one energy source, for instance, at least one ultraviolet lamp 104, having interconnected purification and sterilization functions in the purification and sterilization of air.

In accordance with some embodiments of the present invention, the at least one energy source may be selected from an ultraviolet source, an X-ray source, a Gamma-ray source, and an Alpha-ray source.

The at least one energy source produces rays which demolish biological contaminants depositing on the electrostatic filtering means is inter-displaced within the electrostatic filtering means 102 to have the generated rays in close proximity to the electrostatic filtering means 102 for maximizing the at least one energy source efficiency in demolishing the biological contaminants deposited on the electrostatic filtering means.

In accordance with some embodiments of the present invention, the multi-function air purifying and sterilizing system 100 has a casing 106 having an air inlet 108 at one end of the casing 106, and an air outlet 110 at the other end of the casing 106. Casing 106 may be a box-shaped casing or any other shape.

In accordance with some embodiments of the present invention, the electrostatic filtering means 102 is an electrostatic precipitator (ESP) comprised of a series of conductive members, electrostatic members operating at a first voltage/collecting members and electrostatic members operating at a second voltage/repelling members, such as collecting plates 112A and repelling plates 112B which are configured substantially parallel to the air flow. The collecting plates 112A and the repelling plates 112B may be arranged in an alternating manner. In other embodiments, however, the collecting plates 112A and the repelling plates 112B may be positioned in any other arrangement.

In accordance with some embodiments of the present invention, the collecting plates 112A are configured to operate at a first electrical potential and the repelling plates 112B are configured to operate at a second electrical potential different from that of the collecting plates 112A. For instance, if the collecting plates 112A and the repelling plates 112B are positioned in such a way that the distance in between the plates is about 5 mm, then the repelling plates 112B can be configured to operate at 5 kV, e.g., 1 kV per 1 mm, while the collecting plates 112A are grounded. Such configuration of the plates 112A and 112B allows the creation of an electric field powerful enough to ionize the air molecules and particulate matter such as dust, micro-organisms, and the like.

The electrostatic precipitator further includes ionization wires 113 situated in front of the plates 112A&B. The ionization wires 113 are configured to operate at a relatively high voltage, such as for instance, at 6 kV-13 kV to apply positive charge to the air molecules and the particulate matter at the beginning of the process. As seen in the figure, some of the collecting plates 112A are extended in width to operate with the high voltage ionization wires 113.

The ionization wires 113 receive high voltage and emit ions which ionize air molecules and particulate matter including biological contaminants in the incoming air.

In accordance with some embodiments of the present invention, as the ionized air molecules with the ionized particulate matter and the ionized biological contaminants reach the plates 112A and 112B, the charged particulate matter and biological contaminants are electrostatically attracted to and couple to the collecting plates 112A. The repelling plates 112B repel or otherwise direct the charged particulate matter and biological contaminants towards the adjacent collecting plates 112A due to a difference in electrical potential and/or a difference in electrical charge between the repelling plates 112B and the collecting plates 112A.

In accordance with some embodiments of the present invention, the at least one ultraviolet lamp 104 having a tubular shape is arranged so that its longitudinal direction is orthogonal to the direction of air flow.

The at least one ultraviolet lamp 104 is connected to a power supply socket in the casing 106 and connected to a power source.

In accordance with some embodiments of the present invention, the UV light produced by the at least one ultraviolet lamp 104 demolishes biological contaminants depositing on the plates 112A&B, such as bacteria, viruses and other active micro-organisms.

In contrast to prior purifier designs, the multi-function air purifying and sterilizing system 100 is highly efficient in filtering and sterilizing the incoming air, e.g., separating particulate matter and demolishing biological deposits such as bacterial, viruses and other active micro-organisms contaminants effectively, and thus preventing such bacteria, viruses and other active micro-organisms contaminants from culturing on the plates 112A&B and ejecting back into the room/confined area.

Specifically, the multi-function air purifying and sterilizing system 100, in accordance with some embodiments of the present invention, has a unique configuration according to which the at least one ultraviolet lamp 104 passes through an opening in each of the plates 112A&B, and thus, is in close proximity to the plates 112A&B. Such unique configuration in which the at least one ultraviolet lamp 104 is disposed within the plates 112A&B, e.g., the highly reflective plates 112A&B surround the at least one ultraviolet lamp 104, and thus, increase the effect of the generated UV light in demolishing bacteria, viruses and other active micro-organism contaminants depositing on the plates 112A. More specifically, the highly reflective plates 112A&B, surrounding the at least one ultraviolet lamp 104, reflect the ultraviolet light emitted from the at least one ultraviolet lamp 104, and thus increase the intensity of the UV light, which in turn, increases the efficiency of the destruction of bacteria, viruses and other active micro-organisms and the reaction efficiency between the ultraviolet light and the ozone. The destruction of the micro-organisms deposits highly depends on the duration of contact, e.g., the longer the biological-type deposits are exposed to the UV light, the more successful is the sterilization process. Thus, the close proximity of the at least one ultraviolet lamp 104 to the biological-type deposits and the adjustable flow rate of the incoming air allow for the necessary exposure of the biological-type deposits to the UV light for demolishing such biological-type deposits effectively.

In accordance with some embodiments of the present invention, the plates 112A&B may be made of highly reflective materials, i.e., metals such as aluminum or silver, alloys or other chargeable materials such as, for instance, chargeable polymeric material(s).

The highly reflective plates 112A&B reflect the ultraviolet light emitted from the at least one ultraviolet lamp 104, and thus increase the intensity of the UV light, which in turn, increases the efficiency of the destruction of bacteria, viruses and other active micro-organisms and the reaction efficiency between the ultraviolet light and the ozone.

In accordance with some embodiments of the present invention, the multi-function air purifying and sterilizing system 100 of the present invention allows a secondary sterilization process. While in operation, ozone molecules are produced via the electric field created by the plates 112A&B and mainly via the corona discharge/cold plasma produced by the spikes (seen in FIG. 2). The ozone molecules envelop the at least one ultraviolet lamp 104 and thus force the at least one ultraviolet lamp 104 to alter the molecular structure of the ozone molecules and turn them into hydroxyl radicals.

The hydroxyl radical is antiseptic by acting as a strong oxidizing agent and thus eliminates micro-organisms that are still active and capable of developing and multiplying on the plates 112A&B and within the room/confined space and the like. Thus, the present invention uses ozone, a contaminating by-product, to produce hydroxyl radicals, and thus, to produce a secondary sterilization process to eliminate undesired micro-organisms in the room/confined space. The hydroxyl radicals break down a broad range of odors, gases, and pathogens, and thus, are great for area and content deodorization.

Figure 1B:
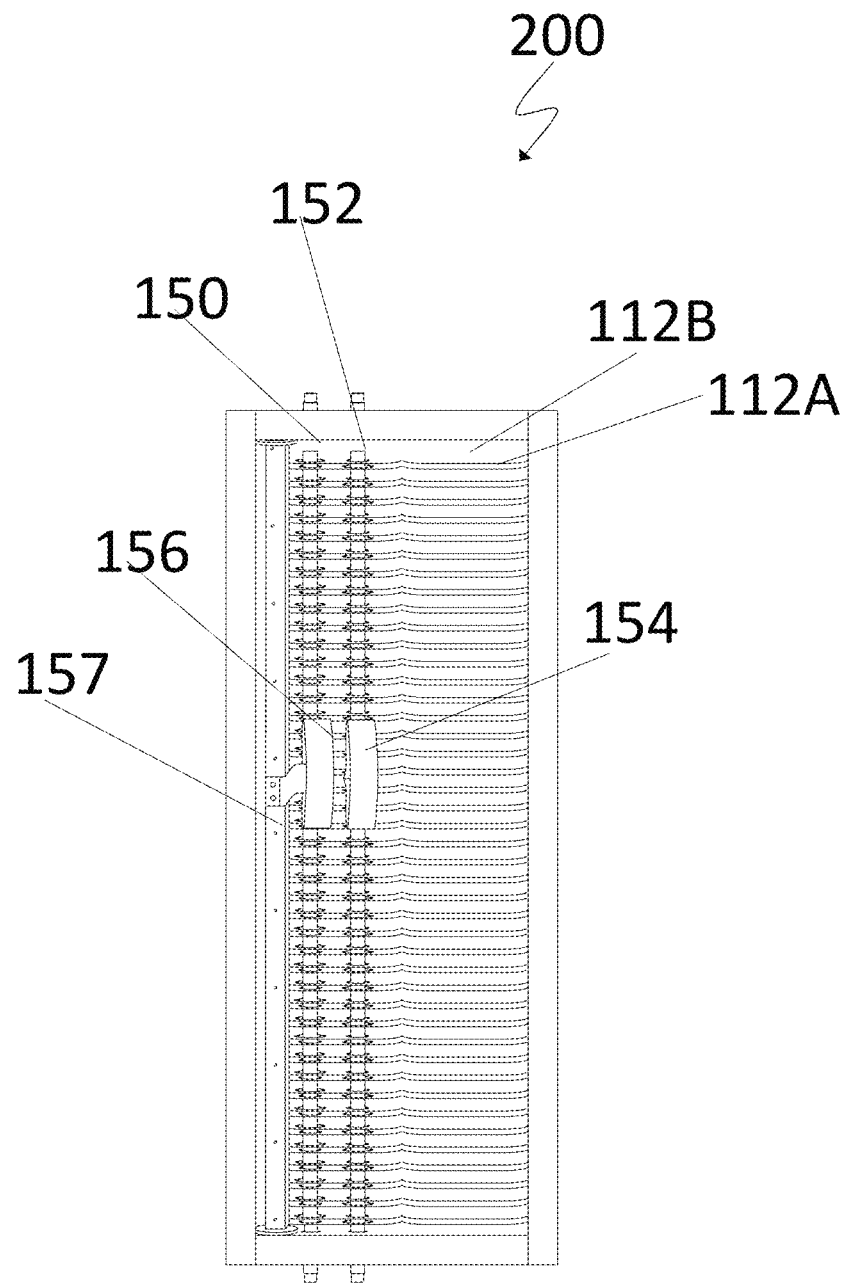

FIG. 1B is a top view of the multi-function air purifying and sterilizing system 100 in accordance with some embodiments of the present invention.

As seen in the figure, a first spacer 150 and a second spacer 152 are passing through all plates 112A&B. Due to the design of the plates 112A&B (as seen and described in FIGS. 2A&B), first spacer 150 passes through all plates 112A&B but is in contact with the collecting plates 112A only, while second spacer 152 passes through all plates 112A&B but is in contact with the repelling plates 112B only. Thus, first spacer 150 keeps collecting plates 112A grounded, and second spacer 152 delivers high voltage to the collecting plates 112A.

Second spacer 152 is connected to arm 154 through which high voltage flows to second spacer 152, and first spacer 154 is connected to arm 156 which is connected to a grounded area 157 in the multi-function air purifying and sterilizing system 100.

Figures 2A, 2B:
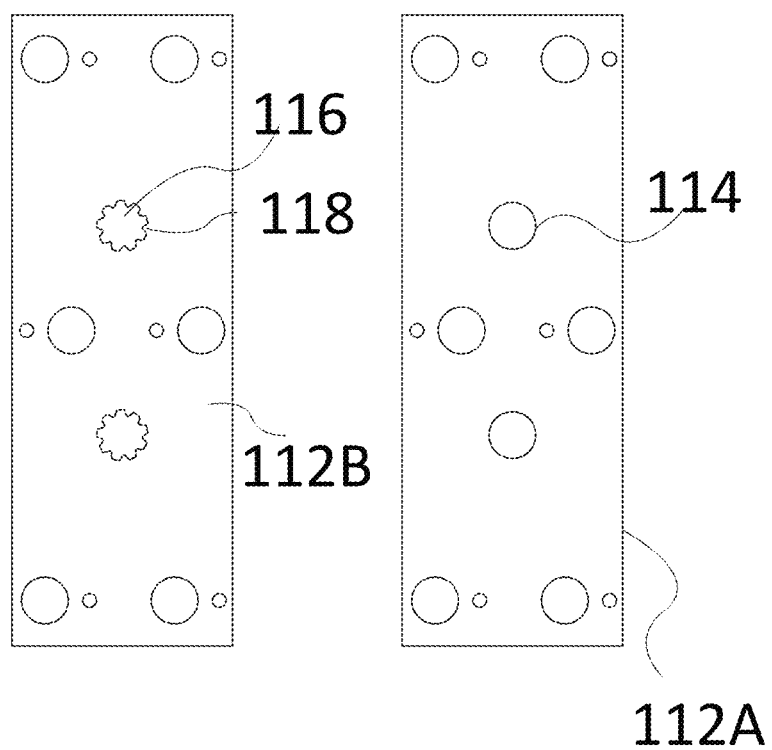

FIGS. 2A&B illustrate a collecting plate 112A and a repelling plate 112B in accordance with some embodiments of the present invention.

As seen in the figures, each of the collecting plates 112A and the repelling plates 112B may be designed to have multiple openings, so that when arranged in a consecutive order, multiple 3D type openings are forming within which multiple ultraviolet lamps 104 seen in FIG. 1A and spacers such as first spacer 150 and second spacer 152 seen in FIG. 1B may be disposed.

In accordance with some embodiments of the present invention, the openings through which spacer 150 and spacer 152 are disposed are of different diameters in order to allow/avoid contact between the plates 112A and 112B and the spacers 150&152.

The openings through which the at least one ultraviolet lamp 104 are disposed may be designed to have either a smooth or a non-smooth surface. In accordance with some embodiments of the present invention, it is preferred that the opening in each of the collecting plates 112A may have a smooth surface 114 while the opening in each of the repelling plates 112B may have a non-smooth opening surface 116, and preferably may comprise multiple spikes 118.

In accordance with some embodiments of the present invention, such spikes 118 are highly essential as corona discharge and/or cold plasma is induced via such spikes 118 when high voltage is applied. The corona discharge and/or the cold plasma leading to the production of a relatively high amount of ozone. More specifically, the corona discharge and/or the cold plasma induced via the spikes 118 at the surface of the opening 116 in each of the repelling plates 112B multiply the amount of the generated ozone which is converted to a hydroxyl radical via the UV light.

Ozone is usually known as an undesired contaminant the production of which requires an implementation of filters placed substantially perpendicular to the airflow. However, since ozone is converted to a hydroxyl radical via the UV light, the production of a significant amount of ozone is highly desired throughout the purification process of the present invention.

The ozone, produced by the plates 112A&B and mainly by the occurrence of spontaneous corona discharge/cold plasma produced by the spikes 118, envelops the at least one ultraviolet lamp 104. The UV light alters the molecular structure of the ozone and thus converts the ozone to a hydroxyl radical. The hydroxyl radical produces a secondary sterilization process—it disinfects and inhibits bacteria and viruses and other active micro-organisms within the room/confined space. It also removes gases and odors. Therefore, the spikes 118 play an important role in such design of the multi-function air purifying and sterilizing system 100 due to the occurrence of spontaneous corona discharge which produces a significant amount of ozone.

Figure 3A:
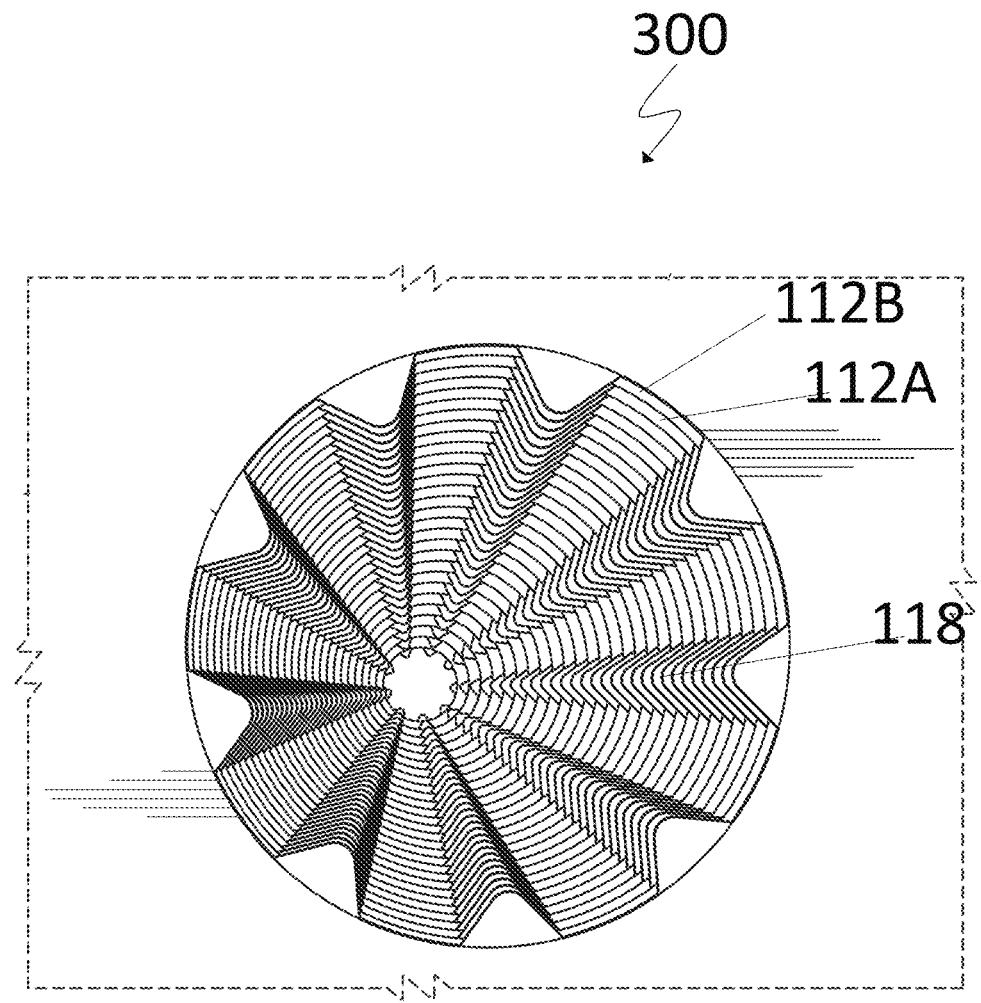

FIG. 3A illustrates a 3D-type opening 300 created by arranging a plurality of plates 112A and 112B in a consecutive order. Also seen in the figure are the spikes 118 of the alternating repelling plates 112B.

Figure 3B:
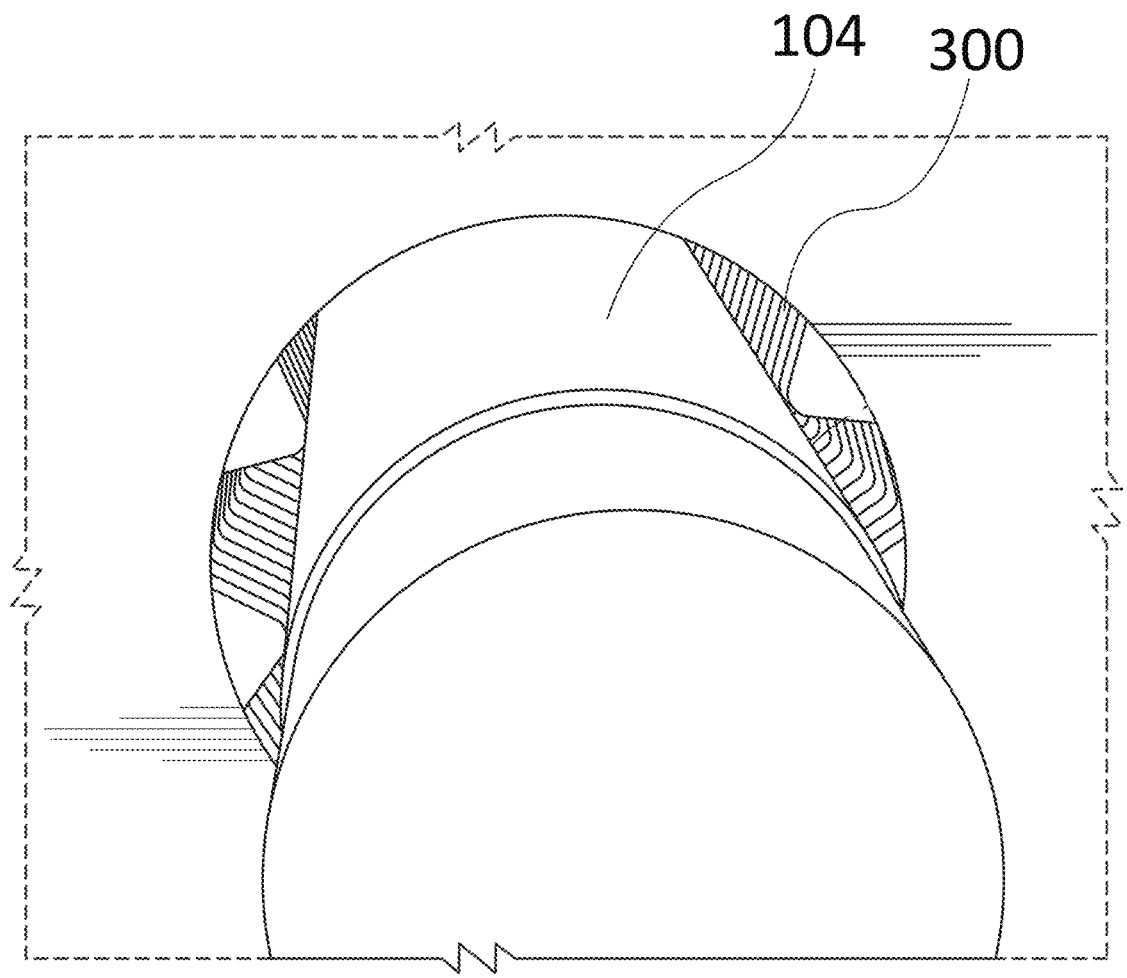

FIG. 3B illustrates the 3D-type opening 300 and an ultraviolet lamp 104 disposed therein.

Figure 4:
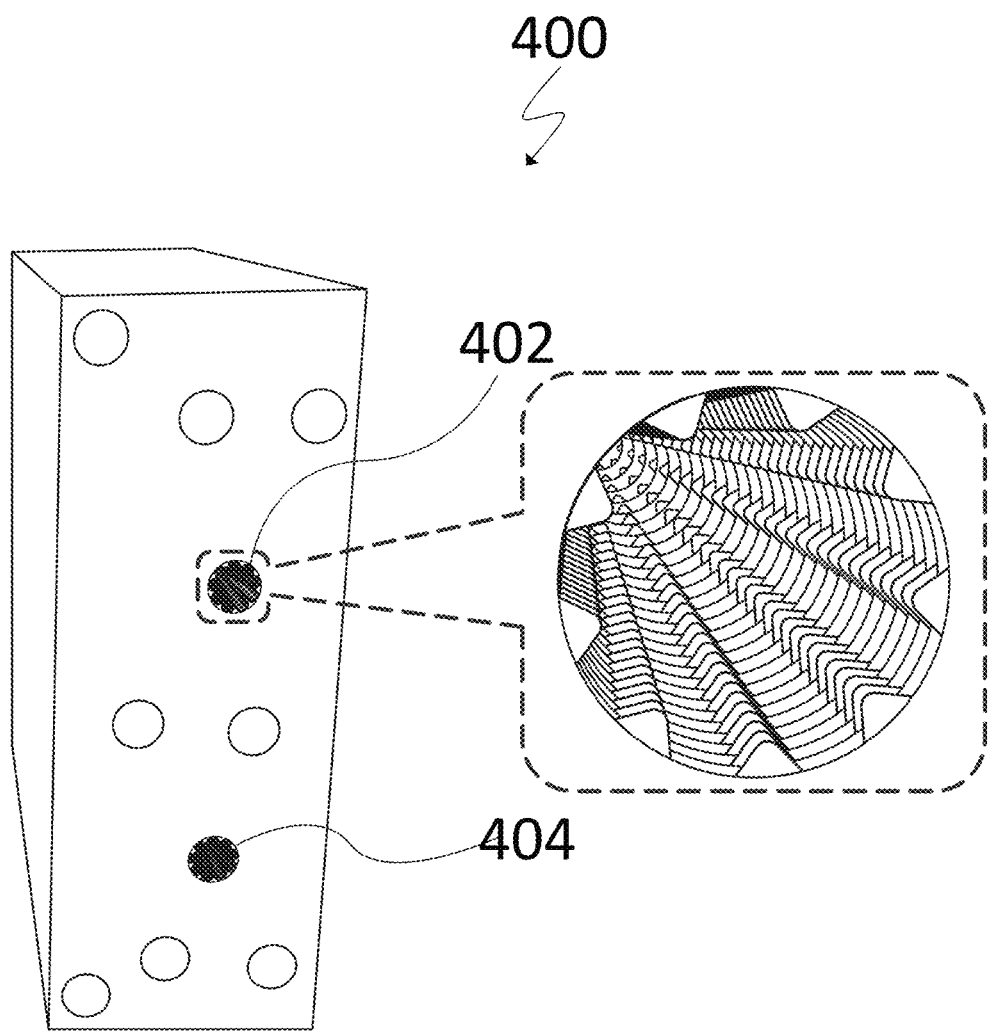

FIG. 4 is a side-view 400 of the multi-function air purifying and sterilizing system 100 in accordance with some embodiments of the present invention. Seen in the figure are openings 402 and 404 of 3D-type openings within which ultraviolet lamps 104 are disposed.

In accordance with some embodiments of the present invention, the role of the plates 112A&B is two-fold: (1) to charge particles such as dust and the like and biological contaminants and divert the particles and the biological contaminants to the collecting plates 112A, and thus, remove the particles and the biological contaminants from the air flow as the air passes through the plates 112A&B and demolish the biological contaminant, and (2) to reflect the UV light emitted from the ultraviolet lamp 104 in order to increase the intensity of the UV light which increases (a) the efficiency of the destruction of biological contaminants such as bacteria, viruses and other active micro-organisms and (b) the reaction efficiency between the ultraviolet light and the ozone molecules.

In accordance with some embodiments of the present invention, the multi-function air purifying and sterilizing system 100 of the present invention is highly efficient as it is capable of removing particles and micro-organisms as small as 0.01 micron sized particles. In accordance with some embodiments of the present invention, the efficiency of the multi-function air purifying and sterilizing system 100 may increase as the flow rate of the air entering the multi-function air purifying and sterilizing system 100 decreases—a decreased air flow rate (a) increases the probability that charged particulate matters and biological contaminants would be electrostatically attracted and coupled to the collecting plates and (b) increases the contact time between the UV light and biological contaminants such as bacteria, viruses and other active micro-organisms deposits.

The flow rate of the air into the multi-function air purifying and sterilizing system 100 may be set by a blower (not shown in the figure) used for flowing air into the multi-function air purifying and sterilizing system 100. The blower may be disposed either in front of or behind the multi-function air purifying and sterilizing system 100 adjacent to the air inlet 108 as seen in FIG. 5 or to the air outlet respectively.

Figure 5:
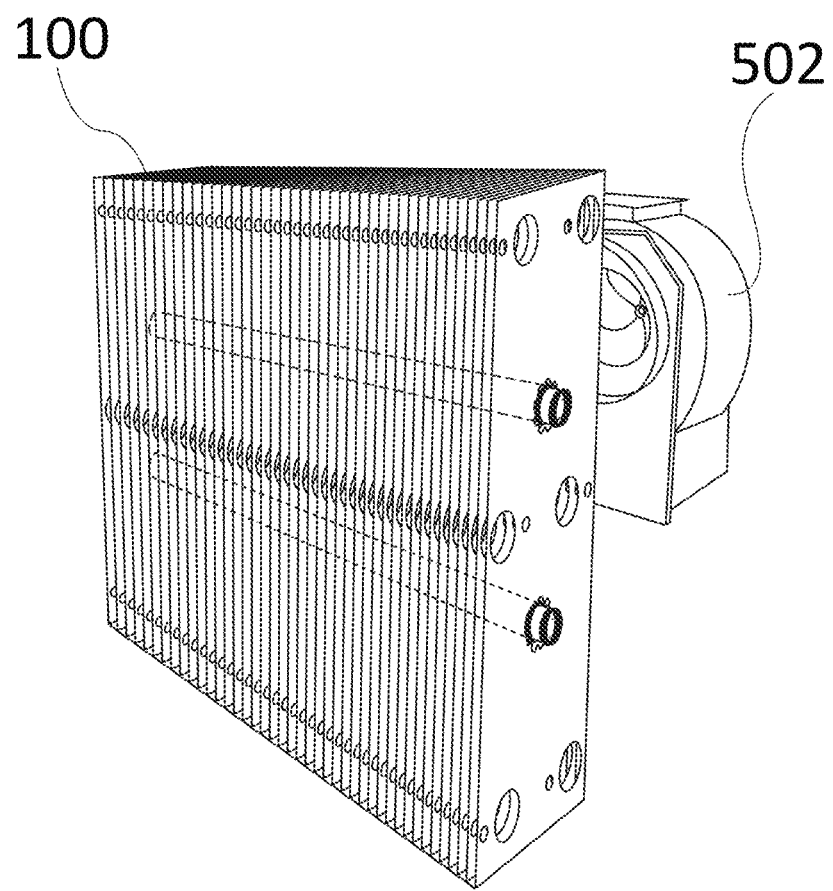

FIG. 5 illustrates a blower 502 disposed in front of the multi-function air purifying and sterilizing system 100 in accordance with some embodiments of the present invention.

In accordance with some embodiments of the present invention, blower 502 may be disposed either in front of or behind the multi-function air purifying and sterilizing system 100.

In accordance with some embodiments of the present invention, at least one of a heating means, cooling means, drying means, and humidifying means may be added to the multi-function air purifying and sterilizing system 100 either internally or externally to improve the efficiency of the purification and sterilization processes.

In accordance with some embodiments of the present invention, the multi-function air purifying and sterilizing system 100 may further comprise at least one sensor for warning of a burned-out UV lamp, and/or at least one sensor indicating whether the multi-function air purifying and sterilizing system 100 is clogged and has to be cleaned.

FIGS. 6A-E illustrate an air purifying process via the multi-function air purifying and sterilizing system 100 in accordance with some embodiments of the present invention.

In FIG. 6A an air stream with particulates and biological contaminants 602 approaching the multi-function air purifying and sterilizing system 100.

In FIG. 6B the air stream with particulates and biological contaminants 602 reaching the multi-function air purifying and sterilizing system 100. As seen in the figure, as the air stream with particulates 602 reaches the multi-function air purifying and sterilizing system 100, it hits ionization wires 604 which apply positive charge to the air and to the particulates at the beginning of the process.

In FIG. 6C, the positively charged air stream with particulates and biological contaminants 604 proceeds towards the plates 112A and 112B and the charged particulates and biological contaminants are electrostatically attracted to and thus electrically coupled to the collecting plates 112A. The repelling plates 112B repel or otherwise direct the charged particulates and biological contaminants towards adjacent collecting plates 112A due to a difference in electrical potential and/or a difference in electrical charge between the repelling plates 112B and the collecting plates 112A.

In FIGS. 6D&E the air stream with positively charged particulates and biological contaminants 604 keeps flowing and the particulates and biological contaminants 604 gradually fill up the collecting plates 112A.

The air stream exiting the multi-function air purifying and sterilizing system 100 is a purified and sterilized air stream 606 free of particulate and biological component.

In accordance with some embodiments of the present invention, in order to extend the service time of the multi-function air purifying and sterilizing system 100, the role of the repelling plates 112B may be reversed with the role of the collecting plates 112A, i.e., the repelling plates 112B which are normally configured to operate at high voltage may be configured to operate at ground, and the collecting plates 112A which normally operate at ground voltage may be configured to operate at High voltage.

Figure 7:
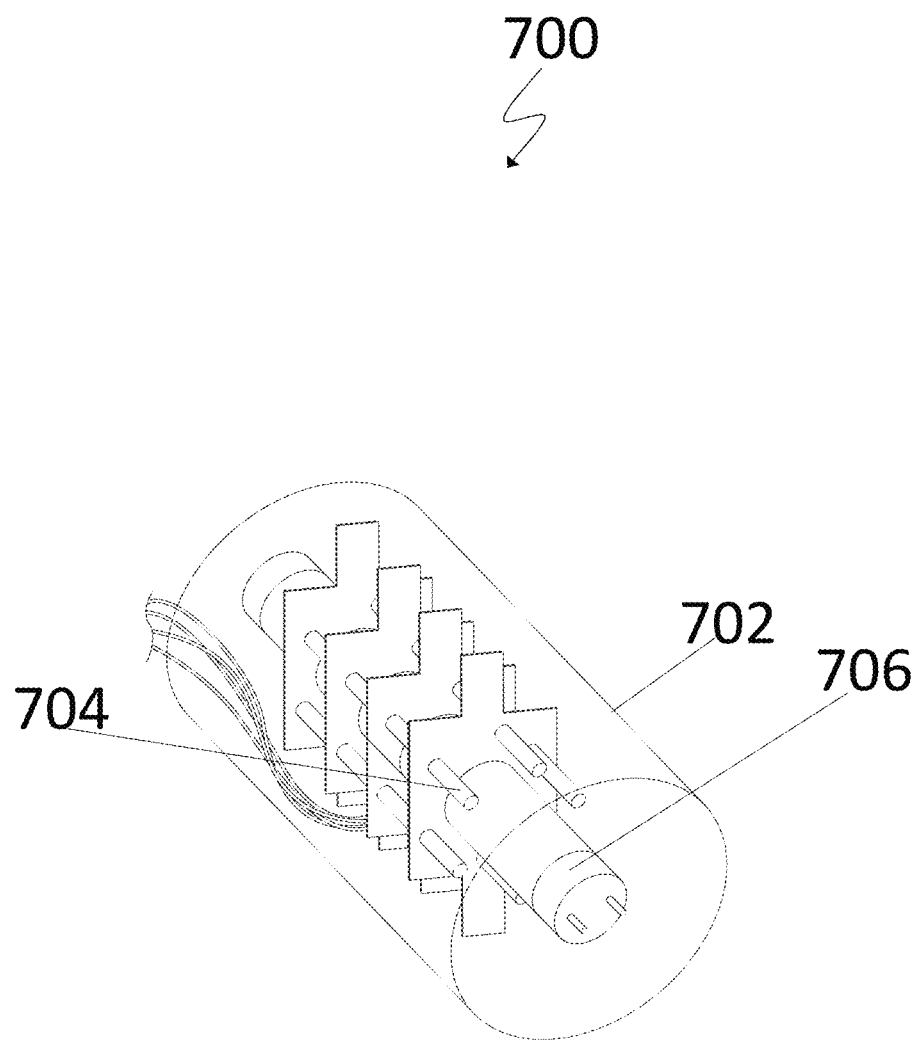
FIG. 7 illustrates a cylinder-shaped multi-function air purification system in accordance with some embodiments of the present invention.

FIG. 7 illustrates a cylinder-shaped multi-function air purification system 700 in accordance with some embodiments of the present invention.

The cylinder-shaped multi-function air purification system 700 comprises electrostatic filtering means, electrostatic precipitator (ESP), and an energy source having interconnected filtering roles in the purification and sterilization of air.

In accordance with some embodiments of the present invention, the at least one energy source may be selected from an ultraviolet source, an X-ray source, a Gamma-ray source, and an Alpha-ray source.

Seen in the figure, the cylinder-shaped multi-function air purification and sterilization system 700 comprises a collecting cylindrical tube 702, a repelling means, such as, for instance at least one ionization rod 704, and an ultraviolet lamp 706 charged with positive high-tension charge.

As seen, the at least one ionization rod 704 envelops the ultraviolet lamp 706.

In accordance with some embodiments of the present invention, the collecting cylindrical tube 702 operates at a first electrical potential and the at least one ionization rod 704 operates at a second electrical potential different from the collecting cylindrical tube 702. For instance, the at least one ionization rod 704 can be configured to operate at high voltage, for instance, at a voltage ranging between 15 kV and 30 kV while the collecting cylindrical tube 702 can be grounded to create an electrostatic precipitator. The at least one ionization rod 704 emits ions which ionize air molecules, particulate matter and biological contaminants in the air flowing through the cylinder-shaped multi-function air purification system 700.

Thus, in accordance with some embodiments of the present invention, an electric field is created via the at least one ionization rod 704 and the collecting cylindrical tube 702 which ionizes air molecules, particulate matter and biological contaminants of the air flow.

In accordance with some embodiments of the present invention, the ionized particulate matter and biological contaminants are propelled by the electrical charge, i.e., electrostatically directed towards the collecting cylindrical metal tube 702. More specifically, the at least one ionization rod 704 repels or otherwise directs the ionized particulate matters and biological contaminants towards the collecting cylindrical tube 702 due to a difference in electrical potential and/or a difference in electrical charge between the at least one ionization rod 704 and collecting cylindrical tube 702.

The UV lamp 706 demolishes the biological contaminants deposited on the cylindrical tube 702 and thus sterilizes the air stream.

In accordance with some embodiments of the present invention, while in operation, air is pushed into the cylindrical tube 702 and the at least one ionization rod 704 applies positive charge to air molecules, particulate matters and biological contaminants. Then, as the air advances in the collecting cylindrical tube 702, the at least one ionization rod 704 repels or otherwise directs the ionized particulate matters and biological contaminants towards the collecting cylindrical tube 702 due to a difference in electrical potential and/or a difference in electrical charge between the at least one ionization rod 704 and collecting cylindrical tube 702.

The UV light demolishes biological contaminants such as bacteria, viruses and other micro-organisms that are still active and capable of developing and multiplying on the collecting cylindrical tube 702.

In addition, the at least one ionization rod 704 producing ozone molecules, and since the at least one ionization rod 704 envelopes the ultraviolet lamp 706, it forces the ultraviolet lamp 706 to turn the ozone molecules into hydroxyl radicals. The hydroxyl radicals are antiseptic by acting as strong oxidizing agents and thus demolish micro-organisms within the room/confined space. The hydroxyl radicals break down a broad range of odors and pathogens, and thus, is great for area and content deodorization.

In accordance with some embodiments of the present invention, the collecting cylindrical tube 702 reflects the UV light emitted via the light lamp 706 and thus increases the intensity of the UV light hitting the active micro-organisms deposits, and thus, increases the sterilization efficiency. Light reflection expands the area of light irradiated, and thus, increases the photocatalytic reaction efficiency between the ultraviolet light and the photocatalytic substance, i.e., the ozone.

The cylinder-shaped multi-function air purification system 700 of the present invention is highly efficient as it is removes particles having a diameter as small as 0.01 micron.

Amongst these particles are micro-organisms that are active and capable of developing and multiplying on the collecting cylindrical tube 702.

In accordance with some embodiments, the collecting cylindrical tube 702 and the at least one ionization rod 704 may be made of a conductive material having high light reflecting efficiency, i.e., metal such as aluminum or silver, alloy or other chargeable materials such as, for instance, chargeable polymeric material (s).

Figure 8A:
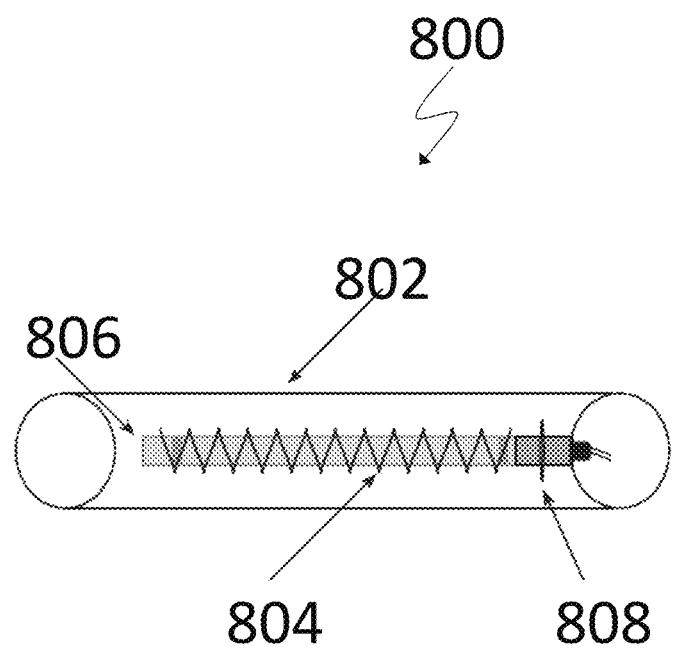
FIG. 8A illustrates an alternative cylinder-shaped multi-function air purification system in accordance with some embodiments of the present invention.

FIG. 8A illustrates an alternative cylinder-shaped multi-function air purification system 800 in accordance with some embodiments of the present invention.

The alternative cylinder-shaped multi-function air purification system 800 in accordance with some embodiments of the present invention comprises a collecting cylindrical tube 802, a repelling metal means which is a conductive wire 804, an ultraviolet lamp 806 charged with positive high-tension charge, and ionization members 808.

In accordance with some embodiments of the present invention, the ultraviolet lamp 806 is wrapped with the conductive wire 804.

In accordance with some embodiments of the present invention, the collecting cylindrical tube 802 operates at a first electrical potential and the conductive wire 804 operates at a second electrical potential different from the collecting cylindrical metal tube 802.

In accordance with some embodiments of the present invention, while in operation, air is pushed into the cylindrical tube 802 and the ionization members 808 apply positive charge to the air.

As the air advances in the collecting cylindrical tube 802, the ionized particulate matters and biological contaminants are propelled by the electrical charge, i.e., electrostatically attracted, towards the collecting cylindrical metal tube 802. The UV lamp demolishes the biological contaminants and thus sterilizes the air stream.

The conductive wire 804 repels or otherwise directs the ionized particulate matters and biological contaminants towards the collecting cylindrical tube 702 due to a difference in electrical potential and/or a difference in electrical charge between the conductive wire 804 and collecting cylindrical tube 802.

The UV light demolishes biological contaminants such as bacteria, viruses and other micro-organisms that are still active and capable of developing and multiplying on the collecting cylindrical tube 802.

The ionization members 808 and the ionization wire 804 producing ozone molecules. The ionization wire 804 enveloping the ultraviolet lamp 806 and thus forcing the ultraviolet lamp 806 to turn the ozone molecules into hydroxyl radicals.

Figure 8B:
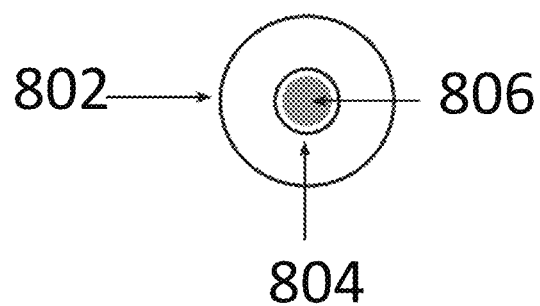
FIG. 8B is a cross-sectional top view of the cylinder-shaped multi-function air purification system of FIG. 8A.

FIG. 8B is a cross-sectional top view of the cylinder-shaped multi-function air purification system 800 of FIG. 8A.

EXAMPLES

The multi-function air purifying and sterilizing system has been examined by a certified laboratory for testing the efficiency of air conditioning and disinfection as well as by a Clinical Microbiology Laboratory.

Experimental Example No. 1

Testing the Multi-Function Air Purifying and Sterilizing System by a Certified Laboratory (ISO13485, ISO 9001, Certified Laboratory)

On 3 Nov. 2020 the multi-function air purifying and sterilizing system was tested by a certified laboratory (ISO13485, ISO 9001, certified laboratory) and has been certified by the North America National Accreditation Board. The test included placement of the multi-function air purifying and sterilizing system inside an active space (5.2×5×5 m), and air sampling was performed by a pumping system before and after operation at different points and distances from the entrance to the system. The room was opened for natural disinfection for one hour for the test days.

The following are the main findings of the test:

| Sampling Day | Day 1 | | | Day 2 | | | | Day 3 |
|---|---|---|---|---|---|---|---|---|
| Number of sampling points(1)/Sampling time | 11:30 AM (2) | 4:30 PM | 8:30 PM | 7:45 AM | 9:00 AM (3) | 2:00 PM | 6:00 PM | 7:45 AM(3) |
| CFU 50 (L): Bacteria + Molds | | | | | | | | |
| A1/2 | 84 + 53 | 10 + 5 | 2 + 2 | 2 | 10 + 20 | 4 + 13 | 1 + 8 | 2 |
| A1/3 | 84 + 36 | 9 | 7 + 5 | 3 | 63 + 23 | 0 | 4 + 1 | 5 |
| A1/5 | 64 + 54 | 2 + 9 | 4 + 4 | 1 | 70 + 22 | 3 + 1 | 4 + 1 | 2 |
| A1/6 | 84 + 16 | 10 + 22 | 17 + 12 | 6 + 3 | 286 + 18 | 12 + 5 | 13 + 8 | 4 + 3 |

(1) The number has no meaning and is used for convenience only.
(2) Taken before operating the system: Sample of bacteria and molds in the sampling room.
(3) Additional sampling point after shutting down the system after running a continuous system overnight.

Figure 9:
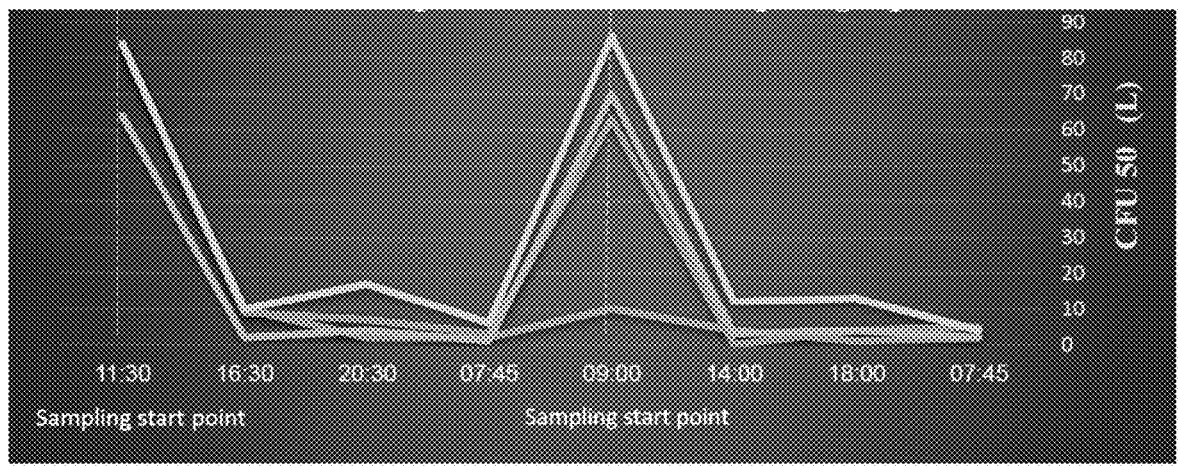
FIG. 9 illustrates bacterial count throughout the trial stages at different points in the sampling space.

FIG. 9 illustrates bacterial count throughout the trial stages at different points in the sampling space.

Figure 10:
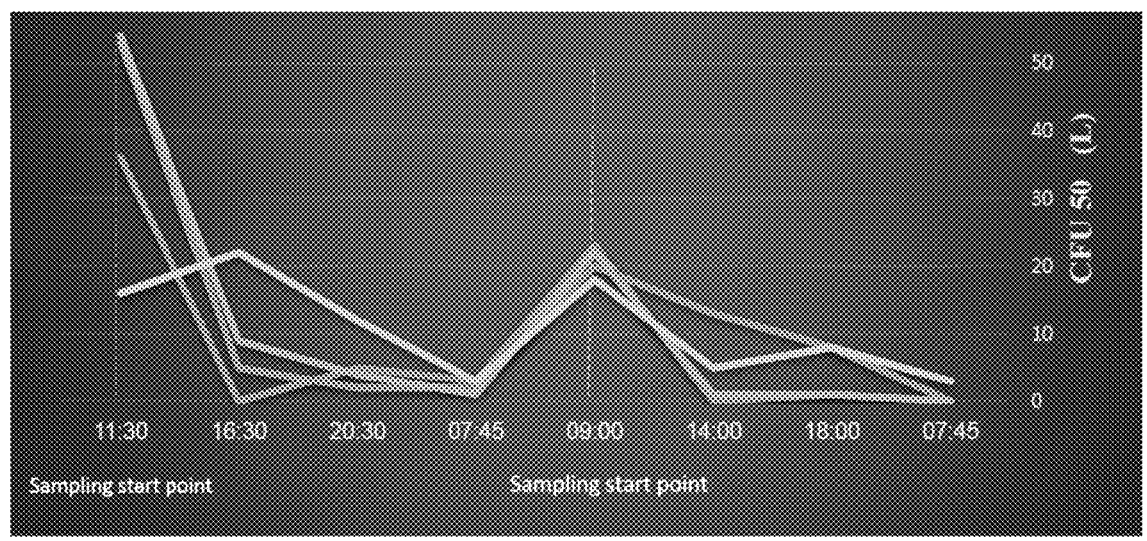
FIG. 10 illustrates mold count throughout the trial stages at different points in the sampling space.

FIG. 10 illustrates mold count throughout the trial stages at different points in the sampling space.

Experimental Example No. 2A

Testing the Multi-Function Air Purifying and Sterilizing System by a Clinical Microbiology Laboratory On 16 Nov. 2020 the multi-function air purifying and sterilizing system was set up in a microbiology laboratory, and over 4 days various points were sampled within the laboratory space, and a bacterial count was performed at different points in the room.

The specific model of the multi-function air purifying and sterilizing system that was tested comprises 2 UV power bulbs each of 16 W and operates at a power of 1,400 m³/hr.

It should be noted that the method of sampling was by placing in the room a plate containing a substrate for growing bacteria (Sheep Blood Agar) for the time during which the system was tested at different points in the room. The plate was incubated for 72 hours at a temperature of 37° C. At the end of the incubation, the colonies that developed on the plate were counted.

During the test period the activity in the room continued as usual. The tests were performed during continuous laboratory work while the door was left open.

Figure 11:
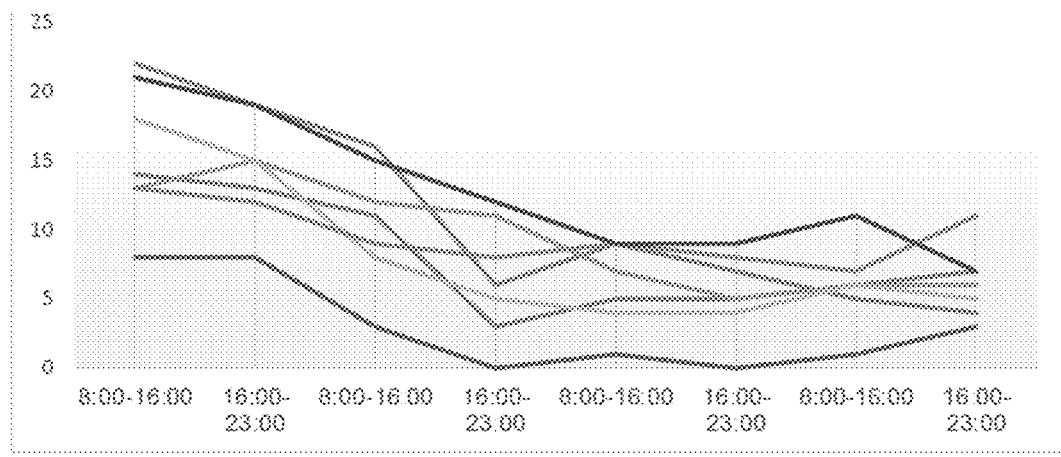
FIG. 11 illustrates bacterial count throughout the trial at different points in the room including the door handles of the laboratory.

FIG. 11 illustrates bacterial count throughout the trial at different points in the room including the door handles of the laboratory.

| Time | 8:00 | 23:00 |
|---|---|---|
| Bacterial count | 18 | 6 |

Conclusions

The multi-function air purifying and sterilizing system exhibits very high sustained efficiency when it comes to purifying molded air and bacteria. The capabilities of the multi-function air purifying and sterilizing system are due to the filtration system, UV and hydroxyl formation. Since this action is effective against various viruses, the system is also expected to be effective against them as well.

Experimental Example No. 2B

Testing the Multi-Function Air Purifying and Sterilizing System by a Clinical Microbiology Laboratory Plates of the type CHROMagar™ C. difficile containing a suspension of the difficile bacterium (ATCCBAA 1382) were used in the experiment.

It should be noted that the difficile bacterium (ATCCBAA 1382) has been specifically selected since this strain is an increased biofilm producer.

| Time | Laboratory table | Desk | Above the refrigerator | Above the fume hood | Inside the showcase | Internal handle of the laboratory door | Keyboard |
|---|---|---|---|---|---|---|---|
| 8:00 AM-4:00 PM (before activation of the system | 22 | 14 | 13 | 18 | 8 | 13 | 21 |
| 4:00 PM-11:00 PM | 19 | 13 | 15 | 15 | 8 | 12 | 19 |
| 8:00 AM-4:00 PM | 16 | 11 | 12 | 8 | 3 | 9 | 15 |
| 4:00 PM-11:00 PM | 6 | 3 | 11 | 5 | 0 | 8 | 12 |
| 8:00 AM-4:00 PM | 9 | 5 | 7 | 4 | 1 | 9 | 9 |
| 4:00 PM-11:00 PM | 7 | 5 | 5 | 4 | 0 | 8 | 9 |
| 8:00 AM-4:00 PM | 5 | 6 | 6 | 6 | 1 | 7 | 11 |
| 4:00 PM-11:00 PM | 4 | 7 | 6 | 5 | 3 | 11 | 7 |

The plates were attached to the vent of the system for predefined periods of time and were incubated under Anaerobic conditions for 72 hours at 37° C.

Test Results

| Plate No. | Without system exposure | Exposure to the system for one hour | Exposure to the system for two hours | Exposure to the system for six hours |
|---|---|---|---|---|
| 1 | $10^8$ | $10^5$ | $10^4$ | $10^2$ |
| 2 | $10^8$ | $10^5$ | $10^4$ | $10^2$ |
| 3 | $10^8$ | $10^5$ | $10^4$ | $10^2$ |
| 4 | $10^8$ | $10^5$ | $10^4$ | $10^2$ |

Conclusions

The multi-function air purifying and sterilizing system shows very high continuous efficiency when it comes to purifying the air from bacteria Including germ-producing bacteria that are a major nuisance to the health system. The multi-function air purifying and sterilizing system capabilities are due to the system filtration, UV and hydroxyl formation. Since this course of action is also effective against various viruses, efficiency is also expected against them.

Experimental Example No. 3

The multi-function air purifying and sterilizing system has been examined to remove odor derived from hydrogen sulfide.

The system was placed in a building into which municipal sewage is discharged, and Hydrogen sulfide values 75.0 to 3.1 and even above 2 were measured.

It should be noted that the Hydrogen sulfide gas is toxic, and beyond the odor nuisance, it can pose an occupational hazard and employee safety.

The multi-function air purifying and sterilizing system lowered the odor level to 0.45 within two hours and stabilized at 0.4.

Conclusions

The multi-function purifying system is highly efficient in lowering the odor in a confined place. It is completely green and based on hydroxyl production.

The multi-function purifying system does not use acids and/or activated carbon. Therefore, removal of hazardous materials and landfilling are not required.

The scope of the present invention is not limited to structures and functions specifically described herein and is also intended to include devices which have the capacity to yield a structure, or perform a function, described herein, such that even though users of the device may not use the capacity, they are, if they so desire, able to modify the device to obtain the structure or function.

Features of the present invention which are described in the context of separate embodiments may also be provided in combination in a single embodiment.

The invention claimed is:

1. A multi-function air purifying and sterilizing system for sterilizing air comprising:
   a casing having an air inlet at one end of the casing and an air outlet at the other end of the casing with an air stream direction from the inlet to the outlet,
   electrostatic members each of which having at least one opening, the opening comprising at least one spiked surface which extends substantially perpendicular or substantially parallel to the air stream direction, said at least one spiked surface inducing corona discharge and/or cold plasma when high voltage is applied, said corona discharge and/or said cold plasma producing ozone molecules,
   at least one energy source for producing rays, said at least one energy source is inter-displaced within said electrostatic members to have the produced rays in proximity to said electrostatic members for:
   (a) maximizing said at least one energy source efficiency in demolishing said particulate matter and/or said biological contaminants depositing on said electrostatic members,
   and/or
   (b) converting said ozone molecules to hydroxyl radicals, said hydroxyl radicals disinfecting and inhibiting said biological contaminants and/or odors, and/or gases in said air stream and/or in a confined space,
   wherein some electrostatic members operating at a first voltage are collecting members, while other electrostatic members comprised of at least one spiked surface operating at a second voltage are repelling members, said at least one spiked surface inducing corona discharge and/or cold plasma when high voltage is applied, said corona discharge and/or cold plasma producing ozone convertible to an hydroxyl radical via UV light or ultraviolet light or X-rays or Gamma-rays, or Alpha-rays,
   said hydroxyl radical disinfects and inhibits biological contaminants,
   thereby, said multi-function air purifying and sterilizing system either filtering and sterilizing the air via said electrostatic members and/or producing ozone molecules convertible to hydroxyl radicals for disinfecting and inhibiting said biological contaminants and/or odors, and/or gases in said air stream and/or in said confined space; and
   wherein said electrostatic members are comprised of a series of electrostatic members, wherein said series of electrostatic members is configured to extend parallel to the direction of the air stream, each of said electrostatic members having at least one opening to allow at least one ultraviolet lamp to be disposed therethrough.

2. The multi-function air purifying and sterilizing system of claim 1, wherein said hydroxyl radicals acting as a strong oxidizing agent and thus eliminating micro-organisms that are active and capable of developing and multiplying on said electrostatic members and/or within a room or confined space, and breaking down a broad range of odors and pathogens.

3. The multi-function air purifying and sterilizing system of claim 1, wherein said at least one energy source is selected from an ultraviolet source, an X-ray source, a Gamma-ray source, and an Alpha-ray source.

4. The multi-function air purifying and sterilizing system of claim 3, wherein said at least one ultraviolet source is an ultraviolet lamp arranged in a way that its longitudinal direction is orthogonal to the direction of said air stream.

5. The multi-function air purifying and sterilizing system of claim 4, wherein the ozone molecules enveloping the at least one ultraviolet lamp and thus forcing said at least one ultraviolet lamp to convert the ozone molecules to hydroxyl radicals.

6. The multi-function air purifying and sterilizing system of claim 1, wherein said electrostatic members comprising collecting members operating at a first voltage and repelling-members operating at a second voltage reflecting the UV light emitting from the at least one light lamp, thus, increasing the intensity of said UV light which in turn increasing the efficiency of demolishing the biological contaminants depositing on said reflective-type collective members and/or increasing the efficiency of converting said ozone molecules to hydroxyl radicals.

7. The multi-function air purifying and sterilizing system of claim 6, further comprises multiple ionization wires situated in front of said electrostatic members, and wherein multiple of said collecting members having an extended width to operate with high voltage ionization wires, and thus, to create an electric field, said electric field charging said air molecules, said particulate matter, and said biological contaminants with a positive charge at an entrance to said multi-function air purifying and sterilizing system.

8. The multi-function air purifying and sterilizing system of claim 1, wherein said electrostatic members are made of metal, metal alloy, chargeable polymeric material(s) or a combination thereof.

9. The multi-function air purifying and sterilizing system of claim 1, wherein at least one opening in each of said electrostatic members operating at a first voltage and wherein said collecting members have a smooth surface.

10. The multi-function air purifying and sterilizing system of claim 6 wherein each of said at least one opening in each of said collecting members and each of said repelling members having a first opening through which a first spacer is disposed and a second opening through which a second spacer is disposed, said first spacer is delivering a first voltage to said repelling members and said second spacer is delivering a second voltage to said collecting members,
wherein said first opening in said collecting members is larger than said first opening in said repelling members, so that when said first spacer passes through said first opening in said collecting members and through said first opening in said repelling members, said first spacer physically contacts said repelling members only, and thus transfers the first voltage to said repelling members operating at a second voltage only, and
wherein said second opening in said repelling members is larger than said second opening in said collecting members, so that when said second spacer passes through said second opening in said repelling members and through said second opening in said collecting members, said second spacer physically contacts said collecting members only, and thus transfers the second voltage to said collecting members only.

11. The multi-function air purifying and sterilizing system of claim 1, wherein said casing is a cylindrical conducting tube, said electrostatic members is an electrostatic precipitator comprised of a collecting cylindrical tube and a repelling members.

12. The multi-function air purifying and sterilizing system of claim 1, wherein said at least one energy source is selected from an ultraviolet source, an X-ray source, a Gamma-ray source, and an Alpha-ray source.

13. The multi-function air purifying and sterilizing system of claim 1, wherein said at least one energy source is disposed along said cylindrical tube and generating rays which demolish said biological contaminants depositing on the collecting cylindrical tube and/or converting said ozone molecules to hydroxyl radicals.

14. The multi-function air purifying system of claim 1 further comprising an internal or external air blower disposed in front of or behind said multi-function air purifying and sterilizing system for pushing or pulling air in or out of said multi-function air purifying and sterilizing system.

15. The multi-function air purifying and sterilizing system of claim 1 further comprising at least one of a heating, cooling, drying and humidifying means either externally or internally to improve the efficiency of the multi-function air purifying and sterilizing system.

16. The multi-function air purifying and sterilizing system of claim 1 further comprising at least one sensor for detecting malfunctions in said blower and/or in at least one of said heating, cooling, drying and humidifying means, and/or at least one sensor for warning of a burned-out UV sterilization lamp.

17. The multi-function air purifying and sterilizing system of claim 1 further comprising at least one sensor for warning of a clogged multi-function air purifying and sterilizing system.

18. The multi-function air purifying and sterilizing system of claim 1 removing particulate matter and demolishing biological contaminants having a diameter as small as 0.01 micron.

* * * * *